(12) United States Patent
Carnazza

(10) Patent No.: US 7,674,592 B2
(45) Date of Patent: Mar. 9, 2010

(54) METHODS FOR TESTING FOR THE DEVELOPMENT OF HUNTINGTON'S DISEASE

(76) Inventor: James A. Carnazza, 45 Putnam Rd., Holden, MA (US) 01520

( * ) Notice: Subject to any disclaimer, the term of this patent is extended or adjusted under 35 U.S.C. 154(b) by 337 days.

(21) Appl. No.: 11/627,978

(22) Filed: Jan. 28, 2007

(65) Prior Publication Data

US 2007/0141631 A1    Jun. 21, 2007

Related U.S. Application Data

(63) Continuation of application No. 10/654,850, filed on Sep. 4, 2003, now abandoned.

(60) Provisional application No. 60/443,397, filed on Jan. 29, 2003, provisional application No. 60/408,184, filed on Sep. 4, 2002.

(51) Int. Cl.
*G01N 33/53*    (2006.01)
*G01N 33/58*    (2006.01)
*G01N 33/74*    (2006.01)

(52) U.S. Cl. ...................................... 435/7.1
(58) Field of Classification Search ............... None
See application file for complete search history.

(56) References Cited

OTHER PUBLICATIONS

Milewich 1989 (Journal of Endocrinology 123:509-518).*
Bonelli et al., 2004. Expert Opin. Pharmacother. 5:767-776.
Piccioni et al. 2001 Brain Research Bulletin 56:215-220.
Eckert 1988. Animal Physiology. pp. 314-320.
Nausieda et al., 1979. Neurology 29: 1605-1609.
Ott et al. 2002.Nournals of Gerontology: Mecial Sciences 57A:M594-M598.
Koller et al., 1982. Neurology 32:547-549.
Heron et al., 2000. Metaboloic Brain Disease 15:267-274.
Bonuccelli 1992. Advances in Biochemical Psychopharmacology 47:149-154.

* cited by examiner

*Primary Examiner*—Daniel E. Kolker
(74) *Attorney, Agent, or Firm*—Antoinette G. Giugliano PC

(57) ABSTRACT

This invention relates to Huntington's disease and more specifically to methods for testing and inhibiting the development of Huntington's disease.

8 Claims, No Drawings

METHODS FOR TESTING FOR THE DEVELOPMENT OF HUNTINGTON'S DISEASE

CROSS-REFERENCE

This application is a continuation of U.S. application Ser. No. 10/654,850, filed Sep. 4, 2003 now abandoned, which claims the benefit of U.S. Provisional Application No. 60/443,397, filed Jan. 29, 2003 and U.S. Provisional Application No. 60/408,184, filed Sep. 4, 2002. The entire teachings of U.S. application Ser. No. 10/654,850 are incorporated herein by reference.

FIELD OF THE INVENTION

This invention relates to Huntington's disease and more specifically to methods for inhibiting the onslaught of the disease in individuals who test positive for an expanded CAG trinucleotide repeat in the gene that codes for the huntingtin protein.

BACKGROUND OF THE INVENTION

Huntington's disease is a degenerative, neurological disease that is almost exclusively inherited from a parent. About 1 in 10,000 people, or total about 30,000 people in the United States currently have Huntington's disease and about 150,000 are at risk of having inherited the disease from a parent. Individuals who are at risk of developing Huntington's disease inherit a gene (HD gene) from a parent that codes for a protein now known as the huntingtin protein. The HD gene, whose mutation results in Huntington's disease, is located on chromosome 4 and is characterized by an expanded trinucleotide repeat made up of cytosine, adenine and guanine (CAG). HD is an autosomal dominant disorder. Specifically the HD gene is located on a non-sex-linked chromosome, which means that men and women are equally at risk of inheriting the HD gene and, if the gene is inherited from just one of either parent, the inheriting individual will inevitably develop the disease.

Whether an individual has inherited the HD gene that leads to the development of the disease can be determined by a direct gene test using blood samples. The genetic test counts the number of CAG repeats in the HD gene region. In individuals who do not exhibit the HD gene, the length of the repeat pattern occurs up to 38 times or less. In individuals who inherit the HD gene, the repeat pattern occurs more than 38 times. Only about 1-3% of individuals who develop Huntington's disease do not inherit the disease from a parent.

Previously it was inevitable that an individual who carried the HD gene would at some point in their lives develop the disease. HD results in the genetically programmed degeneration of neurons. The disease causes nerve cells in the striatum of the basal ganglia located deep within the brain, particularly those in the caudate nuclei and the pallidium, and nerve cells in the cortex of the outer surface of the brain, to degenerate via programmed cell death (PCD). PCD is a regulated process by which selective gene expression leads to cell death. The disease eventually leads to uncontrolled bodily movements, mental deterioration and emotional disturbances.

Previously, there was no known means to treat, prevent or otherwise inhibit the development of the disease in individuals who either carry the HD gene or who have already begun developing the disease. In the latter group, only symptomatic therapies were available to target the ensuing symptoms resulting from brain degeneration.

SUMMARY OF THE INVENTION

It is therefore a primary object of this invention to provide methods for inhibiting the development of Huntington's disease.

It is a further object of this invention to provide methods for determining the optimum time in an individual's life time to beginning an appropriate hormone therapy adapted to inhibit the development of Huntington's disease.

It is a further object of this invention to provide methods for determining the optimum amount of hormone therapy that is adapted to inhibit the development of Huntington's disease.

A preferred method of the invention for inhibiting the development of Huntington's disease in an individual who is at risk of developing the disease, comprises the steps of: determining that the individual exhibits a trinucleotide repeat pattern, consisting of cytosine, adenine, and guanine, is of sufficient number to indicate a risk for developing Huntington's disease; establishing that a serum level of a preselected hormone in said individual is below normal; administering one or more hormones, selected from a group consisting of estrogen, testosterone, their respective precursors, and esters of estrogen, testosterone, and their respective precursors, in amounts sufficient to inhibit development of the disease, wherein the individual typically exhibits an expanded trinucleotide repeat pattern greater than 38. The individual may exhibit repeats higher than 38 including expanded trinucleotide repeat patterns equal to or greater than 43 or even equal to or greater than 63. The individual typically exhibits a huntingtin polyglutamine protein comprising greater than 38 glutamines. To establish that an individual's serum level is below normal, the method may include the step of testing the individual's blood sample by a suitable method such as a polymerase chain reaction.

The method may further comprise the step of predetermining the rate at which one or more of said hormones binds to a polyglutamine located at an end of said huntingtin polyglutamine protein to determine an optimum time to begin said administering step and said sufficient amount of said one or more hormones, wherein said predetermining step comprises the steps of, obtaining one or more samples of a huntingtin polyglutamine protein with known numbers of glutamines; mixing said sample with a labeled estradiol source and a buffering solution; measuring the binding affinity of the labeled estradiol source to the huntingtin polyglutamine protein. The binding affinity is preferably measured with a gamma counter and may be equal to or less than about 50,000 counts per minute.

A preferred method for determining the optimum time for administering a hormone treatment to inhibit the development of Huntington's disease in an individual who is at risk of developing the disease, generally comprises the steps of: determining a plurality of binding affinities of estradiol to a huntingtin polyglutamine protein with known numbers of glutamines; and measuring the serum level of hormone in said individual to determine if said serum level is below normal. The affinity may be measured with a gamma counter and typically is equal to or less than about 50,000 per minute and may be equal to or less than about 40,000 counts per minute. The mixing step may further comprise mixing said labeled hormone source with a buffering solution.

DETAILED DESCRIPTION OF THE PREFERRED METHODS

The invention features methods for testing for and inhibiting the development of Huntington's disease in individuals who carry the HD gene. Specifically the methods of the invention utilize balanced hormone treatment, including estrogen; testosterone; their precursors such as DHEA and progesterone; and their esters to inhibit the onset of HD that is partially characterized by neural degeneration specific to the spiny neuron in the striatum. The disease, which is characterized by an expanded CAG-polyglutamine repeat, typically manifests itself with aging. The juvenile form of the disease has extreme polyglutamine tracts, which may, in some cases, exceed the possibility of hormone prevention. For example, estrogen and testosterone are widely believed to be psychoprotectants and to inhibit other neurodegenerative diseases such as Alzheimer's and Parkinson's disease.

As hormones such as estrogen, testosterone, and their precursors decline with age, the protective effect of these hormones is lost and the HD disease process advances undeterred. Specifically, for example, estrogen declines by 50% in women by approximately 50 years of age and a further 80% following menopause. Testosterone's and estrogen's, and their precursors', effects on brain functions include, but are not necessarily limited to, stimulation of the growth of the dendritic spines on spiny neurons and regulation of dopomenergic, serotonergic, adrenergic and glutamatergic functions. Testosterone, estrogen, and their precursors also increase the synthesis of certain monoamine neurotransmitters, inhibit their degradation, and interact with neurotrophins that stimulate neural growth and survival.

Animal models of transgenic mice have been developed for the mutant HD gene and specifically it is known that these mice that carry this transgenic gene containing the first exon of the mutant HD gene and have the identical function as the human mutant HD gene. The brains of HD patients and animal models of HD have specific abnormalities that are believed to be negatively affected by deficiency of testosterone, estrogen, or their precursors. Abnormalities in monoamingeric neurotransmission are implicated in the disease process. HD pathogenesis suggests that an early excess of dopaminergic activity causes excitotoxic cell death that is followed by a dopaminergic deficiency as neuronal death ensues.

Estrogen's, testosterone's, and their precursors' known anti-dopaminergic action in the striatum enables them to function early in the disease as neuroprotectants. A differential sensitivity to glutamate causes glutamate toxicity that, in turn, affects spiny neurons in the striatum. Expression of the huntingtin polyglutamine expansion in cells exposed to NMDA-type glutamate receptors causes increased excitotoxic cell death when compared to control cells. Estrogen, testosterone and/or their precursors act to suppress mRNA levels of certain NMDA-glutamate receptors and is thus able to protect neurons against glutamate toxicity.

Estrogen, testosterone, and/or their precursors mediate neuroprotection in neurons induced to undergo apoptosis. Apoptosis, or programmed cell death, is generally used by multicellular organisms to eliminate unnecessary or dangerous cells. Apoptosis is normally important to the development of the brain and nervous system, the immune systems and various body tissues. However, in the case of HD, apoptosis leads to excessive degeneration of nerve cells. Apoptosis is induced by the mutant polyglutamine from the huntingtin protein, causing an influx of Ca+ into a cell through the glutamate receptor. Genes are typically essential for PCD and, by blocking the expressed gene products, such as the HD gene product that codes for the huntingtin protein, PCD is inhibited. In this case, estrogen, testosterone and/or their precursors bind to the polyglutamine located on the end of the huntingtin protein to prevent the protein from inducing cell death by preventing aggregate accumulation in the nuclei of these neurons. The ability of estrogen, testosterone, and their precursors to bind to the huntingtin protein decreases as one ages because the production of estrogen, testosterone, and their precursors decreases with age. Since the length of the CAG polyglutamate repeat determines the level of hormone needed to render this protein ineffective in causing cell death, it is best to begin treatment before ones natural reserves of hormone are depleted with age. The extent of treatment with estrogen, testosterone, and/or their precursors will depend on a given individual based on the length of the CAG glutamine repeat in that individual and the stage of the disease.

Elevated monoamine oxidase (MAO) activity in the brain of HD patients is believed to be the basis for the depressive symptoms so often characteristic of HD. Estrogen, testosterone, and their precursors inhibit MAO activity and have an antidepressant action. Estrogen's, testosterone's, and their precursors' ability to increase cerebral blood flow is believed to counter the decreased cerebral and caudate blood flow associated with HD. Estrogen, testosterone, and their precursors serve as brain protectants in this process.

Following is a preferred method for determining the rate of estrogen binding based on the length of the CAG glutamine repeat. Comparable tests can then be used by physicians in a testing regimen in which hormone levels, such as estradiol levels, as well as the poly-glutamine repeat length of the individual are measured to determine the optimum time to begin therapy.

EXAMPLE

Glycerol Bacterial stocks of three different CAG repeat lengths contained within the first exon of Huntingtin and cloned into the PGex vector 2T were used to inoculate overnight cultures of 25 MI containing 50 mg/mL ampicillin. Pgex is a glutathione transferase fusion expression system Amersham Cat#-27-4587-01-. This system allows for the efficient overproduction of a target protein along with the glutathione-S-transferase as a fusion. These cultures were previously grown and DNA preparations of each were made. They were then sequenced using dye terminator sequencing technique and run on an ABI 377 autosequencer. The results show a 23 CAG repeat contained within the first exon of Huntingtin labeled Q23. A 47 CAG repeat contained within the first exon of Huntingtin labeled Q47 and a 63 CAG repeat contained within the first exon of Huntingtin labeled Q63. The bacterial culture used to make this DNA prep was divided in half. Half of it was used for the DNA prep and the other half was used to make the glycerol stock used to inoculate these cultures. After overnight growth at 37 degrees, the cultures were diluted 1:100 (e.g. 1.25 ML into 125 ml of LB containing 50 mg/ml of antibiotic ampicillin) and then allowed to continue to grow into middle log phase 1.5 hours.

At this point, the bacterial cultures were made using 1.0 mM Isopropyl-b-dThiogalactopyranoside (IPTG) by diluting 100 mM IPTG 1:100 (1.25 mL of 100 mM IPTG into 125 ml of growth culture representing approximately 0.6 OD (optical density) at 590 nM using a common light spectrophotometer). These three cultures were then allowed to grow overnight (20 hrs.) at 30 degrees. These cultures were then centrifuged at 600 rpm for 30 minutes to collect the bacteria. The bacterial pellets were then transferred to a 1.5 mL conical centrifuge tube and 1.0 mL of ice cold PBS (phosphate buffered saline) was added and the pellets dissolved by vortexing for five minutes. This was then split into two 1.5 mL conical tubes containing 700 uL each for all three bacterial preps and then 350 uL of 3% N-lauyl sacosine was added to each of the six tubes, mixed, and then each tube was sonicated for a total of 30 seconds using a Fisher probe sonicator Model number F-50. Next the six tubes were centrifuged in a microfuge top speed for 10 minutes.

The bacterial supernatant of a rich brown color was added directly to the equivalent of 400 uL of Glutathione Sepharose 4B (strict affinity for the glutathione portion of the fusion—target protein over produced) beads washed with ten bead volumes of ice cold PBS. The bacterial supernatant, as a slurry with the Glutathione sepharose, was allowed to gently rock for 30 minutes. After the binding was complete, the bead slurry was centrifuged at 200 rpm 20 seconds to pellet the bead and then repetitively washed five times with two bead volumes with ice cold PBS. After the last supernatant was removed and discarded, the beads were subjected to elution with 10 mM reduced glutathione in 50 mM tris Ph 8.0 by allowing incubation for 10 minutes under gentle shaking. These were then centrifuged 30 seconds at 200 rpm and the elute removed and saved to a new tube. Next, 20 ul of protease inhibitor was added PMSF. Then 30 ul of these were then subjected to polyacylamide gel electrophoresis (PAGE) 12% gels overnight at 90 volts constant voltage.

The next day the gels were stained with coomassie brilliant blue in 50% methanol and 10% acetic acid, for two hours at 50 degrees, and then further destained in the same solution composition minus the coomassie blue for up to four hours. The resultant image shows purification of all three mutant huntingtin protein bands.

These pure proteins were then used in the following binding protocol. Oestradiol-6-(0-carboxymethyl)oximino-(2-[125I]iodohistamine was used as the estradiol source. Buffer B preferably comprises: 250 mM tris, 150 mM NaCl, and a Dextran Charcoal solution comprising 0.05% Dextran coated charcoal in buffer B (sigma Cat#6197). About 0.5 ml of buffer B was preferably used per reaction. A total of 5 ml of Buffer B was aliquoted into a glass borosilicate tube (Fisher Cat#14-961-26) and 10 ul of Oestradiol (I 125) was added containing approximately 2,000,000 cpm. About 0.5 ml of this solution was then distributed into eight labeled glass tubes (cat # 14-961-260). The entire tube #1's 500 uL was counted. Tube #2 through #8 were treated in the following manner:

Tube #1 Total cpm in 0.5 mL of cocktail.
Tube #2 zero/0.5 mL cocktail
Tube #3 Q23/0.5 mL cocktail+50 ul Eluate 1
Tube #4 Q23/0.5 mL cocktail+50 ul Eluate 1
Tube #5 Q47/0.5 mL cocktail+50 ul Eluate 3
Tube #6 Q47/0.5 mL cocktail+50 ul Eluate 3
Tube #7 Q63/0.5 mL cocktail+50 ul Eluate 5
Tube #8 Q63/0.5 mL cocktail+50 ul Eluate 5

Tubes #2-#8 were incubated for 1 hour at room temperature, placed on ice for ten minutes, and 200 uL of the Dextran charcoal solution in buffer B was added. These tubes were then placed on ice ten minutes and then centrifuged 15 minutes at 2200 rpm in a Sorvall RC-3 refrigerated centrifuge with swinging bucket rotor (Sorvall HL-8) at 4 degrees. The entire 700 uL supernatant was removed and counted using Genesys multi-well gamma counter (Laboratories Technology, Inc.) The results are summarized below:

Counts per minute (cpm):

| Total: | 184,972 | (I 125) estradiol in buffer B (count entire tube) |
|---|---|---|
| Zero: | 27,388 | Charcoal Filtered, count supernatant only |
| Sample HD Q23: | 50,107 | + HD Q23, Charcoal Filtered, Count Sup. |
| Sample HD Q23: | 53,797 | + HD Q23, Charcoal Filtered, Count Sup. |
| Sample HD Q47: | 47,454 | + HD Q47, Charcoal Filtered, Count Sup. |
| Sample HD Q47: | 44,767 | + HD Q47, Charcoal Filtered, Count Sup |
| Sample HD Q63: | 38,221 | + HD Q63, Charcoal Filtered, Count Sup. |
| Sample HD Q63: | 38,040 | + HD Q63, Charcoal Filtered, Count Sup. |

The significance of these data is that an affinity for estradiol has been demonstrated using the mutant form of huntingtin, the causative protein in Huntington's disease. It is therefore now applicable that Huntington Disease patients and their at-risk family members should have their polyglutamine repeat length tested and if recognized, to start on a regimen of estradiol, or related hormone, replacement therapy as soon as their normal level of these hormones drop below physiologic levels. Physicians should set up a testing regimen that would determine both estradiol levels as well as the poly-glutamine repeat length to determine the optimum time to begin therapy. It is thereby shown that estradiol is the limiting factor in the progression of Huntington's disease. The estradiol level, or the serum level of other applicable hormones, in conjunction with the known CAG repeat length of affected individuals, is therefore predictive of the symptomatic onset of Huntington's Disease and thus will establish the optimum time in the individual's life to begin administering the appropriate hormone therapy.

Although specific features of the invention are described in connection with some of the preferred methods and not others, this is for convenience only as some feature may be combined with any or all of the other features in accordance with the invention.

Other embodiments will occur to those skilled in the art and are within the following claims:

What is claimed is:

1. A method of binding estrogen to huntingtin (HD) protein, in vitro, wherein the method comprises:
 a) contacting estrogen with the HD protein to thereby allow formation of a complex between estrogen and the HD protein, and
 b) determining the presence or absence of the complex, wherein the complex is labeled.

2. The method of claim 1, wherein the HD protein has at least 23 poly-glutamine repeats.

3. The method of claim 1, wherein the HD protein has at least 38 poly-glutamine repeats.

4. The method of claim 1, further including determining the level of the complex, as compared to a sample that lacks HD protein.

5. A method of determining the presence or absence of a complex between estrogen and huntingtin protein in vitro, wherein the method comprises:
 a) contacting labeled estrogen with the HD protein to thereby allow formation of a complex between estrogen and the HD protein; and
 b) determining the presence or absence of the complex.

6. The method of claim 5, further including determining the level of the complex, as compared to a sample that lacks HD protein.

7. The method of claim 6, wherein the HD protein has at least 23 poly-glutamine repeats.

8. The method of claim 7, wherein the HD protein has at least 38 poly-glutamine repeats.

* * * * *